United States Patent [19]

Tsuji

[11] 4,335,096
[45] Jun. 15, 1982

[54] ABSORBENT FOR USE IN PASSIVE AGGLUTINATION TEST

[75] Inventor: Yoshikatsu Tsuji, Kawasaki, Japan

[73] Assignee: Fujizoki Pharmaceutical Co., Ltd., Tokyo, Japan

[21] Appl. No.: 188,894

[22] Filed: Sep. 19, 1980

Related U.S. Application Data

[63] Continuation-in-part of Ser. No. 122,998, Feb. 20, 1980, abandoned.

[30] Foreign Application Priority Data

Feb. 22, 1979 [JP] Japan ................................ 54/19092

[51] Int. Cl.$^3$ .......................... G01N 1/28; G01N 1/34; G01N 33/50; G01N 33/54
[52] U.S. Cl. .................................... 424/12; 23/230 B; 252/408; 424/8; 424/85; 424/88; 424/92; 424/101; 424/154; 424/359
[58] Field of Search .......................... 424/8, 12, 85–92, 424/101, 154, 358, 359; 23/230 B; 252/408

[56] References Cited

U.S. PATENT DOCUMENTS 3,553,310  1/1971  Csizmas .................................. 424/8

OTHER PUBLICATIONS

Clarke, Amer. J. Trop. Med. Hyg., vol. 7, 1958, pp. 561–572.
Williams, Methods in Immunol. & Immunochem., Acd. Press, NY, vol. I, 1967, pp. 70, 71, 365–370, vol. V, 1976, pp. 61, 62.

Primary Examiner—Anna P. Fagelson
Attorney, Agent, or Firm—Wyatt, Gerber, Shoup, Scobey & Badie

[57] ABSTRACT

Absorbent for use in passive agglutination test which is aldehyde fixed animal erythrocytes or microorganism cells mixed with aluminum hydroxide and calcium phosphate.

11 Claims, No Drawings

ABSORBENT FOR USE IN PASSIVE AGGLUTINATION TEST

This is a continuation-in-part of application Ser. No. 122,998, Feb. 20, 1980 now abandoned.

BACKGROUND OF THE INVENTION

Passive and reverse passive agglutination tests are well known serological procedures.

The usual carriers are erythrocytes of animals, i.e. birds or mammals, or cells of microorganisms. These carriers may have absorbed antigen or antibodies and are known as sensitized cells. Sensitized cells will undergo agglutination reactions with complementary reagents, containing either antibodies or antigens. The agglutination test is a method for optically testing the presence of antigens or antibodies. The agglutinated reaction product will eventually flocculate and precipitate to the bottom of the test vessel.

Agglutination tests are widely employed. They are, however, subject to some difficulty because of an undesirably high number of false positive reactions due to the presence of cross-reacting substances. There are a number of factors which cause these non-specific reactions which give rise to false positives. Typically, they may be antibodies which react with the carrier erythrocytes or cells. Collectively, these factors are, hereinafter, referred to as "anti-carrier". In order to limit the number of false positives, attempts are made to remove anti-carriers by absorption as a routine procedure prior to application of the passive agglutination test.

The absorption removal of anti-carrier is a well known technique. Normally, the absorbents are the same erythrocytes or cells used as carriers. Typically, they are erythrocytes from birds or mammals, although erythrocytes from reptiles or crustaceans may also be employed. All such erythrocytes are referred to herein as animal erythrocytes. The most widely employed are from chickens, turkeys, sheep, cattle, pigs, rabbit or humans. Erythrocytes from chickens and cattle are generally preferred because of their ready availability.

The preferred cellular microorganisms are those such as *Saccharomyces cerevisiae* and *Serratia marcescens*.

The absorbents are aldehyde fixed by, for example, immersion in 0.1% to 30% aqueous formaldehyde solutions at a temperature of from 4° C. to 40° C. for from one to 200 hours. Equivalent aldehyde fixation procedures employing, for example, acetaldehyde, gluteraldehyde or pyruvaldehyde are also known and can be employed in the practice of this invention.

Experience has established two principal difficulties with conventional absorbents. These are, (1) they do not remove all of the interfering reactants, and (2) the products produced by the reaction are difficult to remove, even with a high speed centrifuge. Accordingly, conventional absorbent procedures have not proved entirely satisfactory.

It is, therefore a principal object of this invention to provide novel absorbents which can be used to remove substantially all of the anti-carriers and other factors which interfere with the specificity and reliability of the passive agglutination test.

SUMMARY OF THE INVENTION

The absorbents of this invention comprise aldehyde fixed animal erythrocytes and microorganism cells together with aluminum hydroxide and calcium phosphate. More particularly, the absorbents of the invention are carriers comprising animal erythrocytes or microorganism cells and, on a dry weight basis, from 100 to 400 parts by weight of aluminum hydroxide and 50 to 200 parts by weight of calcium phosphate for every 100 parts by weight of carrier. The preferred form of calcium phosphate is calcium secondary phosphate ($CaHPO_4$ or $CaHPO_4.2H_2O$) but calcium tertiary phosphate ($Ca_3(PO_4)_2$) may also be employed.

The absorbents can be used alone, or together with inert excipients such as starch, clay, talc and the like. They may be used in powder or particulate form. It is convenient, however, to press them, together with the inert excipient, into tablets or other test unit forms providing sufficient active material for a selected number of tests.

The aluminum hydroxide gel utilized in the invention is prepared in any convenient manner. For example, it can be formed by the addition of aqueous sodium or ammonium hydroxide to an aqueous solution of an aluminum salt such as aluminum sulfate or alum to precipitate an aluminum hydroxide in gel form which may be collected by filtration.

150 g to 600 g of aluminum hydroxide gel may be mixed with 30 g to 120 g of powdered calcium phosphate, and the resulting mixture stirred into 100 g of a paste of aldehyde fixed erythrocytes or microorganism cells.

The mixture is next lyophilized under vacuum and pulverized to produce products of the invention in powder form. The absorbent in a tablet form can be prepared by adding 300 g to 500 g of an inert excipient such as starch to the mixture obtained above, and pressing into tablets.

PREFERRED EMBODIMENTS (1) Preparation of aldehyde fixed erythrocytes or microorganism cells.

Erythrocytes were obtained conventionally by sedimentation after an anticoagulant was added to the blood gathered from animals and then plasma was removed by centrifugation. Cells were also obtained by conventional procedures by gathering microorganisms cultured in a medium. Commercial dry yeasts can be utilized in the present invention. The erythrocytes or the cell thus obtained were washed with a physiological saline solution or a phosphate buffer solution. To 100 g of a paste of the erythrocytes or the cells were added 100 ml to 1000 ml of a 0.1% to 30% aqueous solution of formaldehyde, and the mixture was left to stand at a temperature of 4° C. to 40° C. for one to 200 hours to fix the erythrocytes or the cells. The fixed erythrocytes or cells were washed with a physiological saline solution or a phosphate buffer solution, and centrifuged to obtain a paste with water content of about 40%.

(2) Preparation of aluminum hydroxide gel.

860 g of alum was dissolved in 10 l of water, and to the solution was added dropwise 1 N aqueous solution of NaOH to adjust a pH of the solution to 5.2. The precipitate of $Al(OH)_3$ produced was filtered and washed with a phosphate buffer solution to obtain a paste of aluminum hydroxide gel containing about 60% water.

(3) Preparation of tablets of absorbent.

Into 100 g of paste of the fixed erythrocytes (or cells) prepared as described above were mixed 265 g of the paste of aluminum hydroxide gel, 40 g of calcium phosphate ($CaHPO_4.2H_2O$) and 300 g of potato starch. The mixture was lyophilized under vacuum for 30 hours, and then pulverized to provide a brown powder of active absorbent. To 100 g of the powder thus obtained was added 2 g of talc. The mix was thoroughly blended and pressed into tablets each weighing 43 mg. In one tablet, 5 mg of the fixed erythrocytes (or cells) is contained.

ABSORPTION TESTS

The absorbents prepared as described above were evaluated by measuring the effects of absorption, using absorbents from chicken erythrocytes as follows:

One tablet (43 mg) of the absorbent obtained above was added to 0.5 ml of a diluent (a mixture containing rabbit serum in the concentration of one percent by volume in 0.15 M phosphate buffered saline solution) to obtain a dispersion. To the dispersion was added 0.05 ml of anti-chicken serum (i.e. anti-chicken erythrocyte immune serum obtained by rendering immune to rabbit with chicken erythrocytes). The Mixture was stirred to assist absorption and centrifuged to obtain a supernatant. This supernatant is anti-chicken serum from which the anti-carrier and other factors have been removed, and the anti-chicken serum has been diluted ten times with the diluent (phosphate buffered saline solution). 50 μl of the anti-chicken serum were diluted 1:20 to 1:1280 with the diluent. Agglutination tests of the diluted anti-chicken sera were carried out with fixed chicken erythrocytes.

For comparison purposes, agglutination tests were carried out by repeating the procedure described above except that (1) aldehyde fixed chicken erythrocytes (5 mg) were used as an absorbent instead of the absorbent of the invention and (2) no absorbent was used.

The results of the tests are given below:

| | Absorbent | Dilution | | | | | | |
|---|---|---|---|---|---|---|---|---|
| | | 1:20 | 1:40 | 1:80 | 1:160 | 1:320 | 1:640 | 1:1280 |
| anti-chicken serum | Absorbent of the invention | + | − | − | − | − | − | − |
| | Fixed chicken erythrocyte | ++ | + | − | − | − | − | − |
| | No absorbent | ++ | ++ | ++ | ++ | ++ | + | − |

− not agglutinated
+ slightly agglutinated
++ agglutinated

Additional agglutination tests were carried out by repeating the procedure described above except that (1) serum of a patient who had been subjected to external dialysis of the blood, (2) citrated normal human plasma, and (3) heparin treated human plasma were used instead of the anti-chicken serum as described above.

The results of the tests are given below:

| Serum or plasma | Absorbent | Dilution | | | | | | |
|---|---|---|---|---|---|---|---|---|
| | | 1:20 | 1:40 | 1:80 | 1:160 | 1:320 | 1:640 | 1:1280 |
| Serum of patient | Absorbent of the invention | − | − | − | − | − | − | − |
| | Fixed chicken erythrocytes | ++ | + | − | − | − | − | − |
| | No absorbent | ++ | ++ | + | − | − | − | − |
| Citrated plasma | Absorbent of the invention | − | − | − | − | − | − | − |
| | Fixed chicken erythrocytes | ++ | + | − | − | − | − | − |
| | No absorbent | ++ | ++ | + | − | − | − | − |
| Heparin-added plasma | Absorbent of the invention | − | − | − | − | − | − | − |
| | Fixed chicken erythrocytes | ++ | + | − | − | − | − | − |
| | No absorbent | ++ | ++ | + | − | − | − | − |

The absorbents of the invention were also evaluated using anti-sheep serum (i.e. anti-sheep erythrocyte immune serum obtained by rendering immune to rabbit with sheep erythrocytes).

Agglutination tests were carried out by repeating the same procedure described above except that anti-sheep serum and fixed sheep erythrocytes were used instead of anti-chicken serum and fixed chicken erythrocytes.

The results of the tests are given below:

| | Absorbent | Dilution | | | | | | |
|---|---|---|---|---|---|---|---|---|
| | | 1:20 | 1:40 | 1:80 | 1:160 | 1:320 | 1:640 | 1:1280 |
| Anti-sheep serum | Absorbent of the invention | ++ | + | + | − | − | − | − |
| | Fixed sheep erythrocytes | ++ | ++ | ++ | + | − | − | − |
| | No absorbent | ++ | ++ | ++ | +30 | ++ | + | − |

From consideration of the above results, it will be seen that the absorbents of the invention comprising fixed erythrocytes, aluminum hydroxide and calcium phosphate are superior to conventional erythrocyte absorbents in the absorption of factors which cause nonspecific reactions in the passive agglutination test.

The absorbents of the present invention, after reaction, are easily separated and removed from the serum by centrifugation.

It was found by comparison tests that similar absorbents prepared from *Saccharomyces cerevisiae* or *Serratia marcescens*, aluminum hydroxide and calcium phosphate were superior to conventional fixed microorganism cell absorbents.

What is claimed is:

1. An absorbent for use in passive agglutination tests comprising erythrocytes of animals or cells of microorganisms fixed with an aldehyde and, on a dry weight basis, for every 100 parts by weight of carrier, from 100 to 400 parts by weight of aluminum hydroxide and 50 to 200 parts by weight of calcium phosphate.

2. An absorbent of claim 1 dispersed in an inert excipient.

3. A tablet comprising an absorbent of claim 1 dispersed in an inert excipient.

4. An absorbent of claim 1 wherein the erythrocytes are selected from the group consisting of erythrocytes from chickens, turkeys, sheep, cattle, pigs, rabbits and humans.

5. An absorbent of claim 1 wherein the cells are selected from the group consisting of cells from *Saccharomyces cerevisiae* and *Serratia marcescens*.

6. An absorbent according to claim 1 wherein the calcium phosphate is calcium secondary phosphate.

7. An absorbent according to claim 1 wherein the calcium phosphate is calcium tertiary phosphate.

8. An absorbent according to claim 4 wherein the calcium phosphate is calcium secondary phosphate.

9. An absorbent according to claim 4 wherein the calcium phosphate is calcium tertiary phosphate.

10. An absorbent according to claim 5 wherein the calcium phosphate is calcium secondary phosphate.

11. An absorbent according to claim 5 wherein the calcium phosphate is calcium tertiary phosphate.

* * * * *